United States Patent
Linder

(10) Patent No.: US 7,701,206 B2
(45) Date of Patent: Apr. 20, 2010

(54) METHOD AND A DEVICE FOR NON-CONTACT ELECTROMAGNETIC MEASUREMENT OF PROPERTIES OF OBJECTS

(75) Inventor: Sten Linder, Västerås (SE)

(73) Assignee: ABB AB, Västerås (SE)

( * ) Notice: Subject to any disclaimer, the term of this patent is extended or adjusted under 35 U.S.C. 154(b) by 294 days.

(21) Appl. No.: 10/585,127

(22) PCT Filed: Dec. 22, 2004

(86) PCT No.: PCT/SE2004/001983

§ 371 (c)(1),
(2), (4) Date: Nov. 17, 2008

(87) PCT Pub. No.: WO2005/064269

PCT Pub. Date: Jul. 14, 2005

(65) Prior Publication Data

US 2009/0058408 A1    Mar. 5, 2009

(30) Foreign Application Priority Data

Dec. 31, 2003  (SE) .................... 0303610

(51) Int. Cl.
*G01N 27/72* (2006.01)
*G01R 33/12* (2006.01)

(52) U.S. Cl. ............ 324/229; 324/243; 324/227; 324/232

(58) Field of Classification Search ............ 324/229
See application file for complete search history.

(56) References Cited

U.S. PATENT DOCUMENTS

| 4,006,405 | A | * | 2/1977 | Greenwood et al. ........ 324/227 |
| 4,271,393 | A | | 6/1981 | Hansen et al. |
| 4,639,669 | A | * | 1/1987 | Howard et al. ............ 324/239 |
| 4,818,936 | A | * | 4/1989 | Kemlo ................... 324/232 |
| 5,059,902 | A | | 10/1991 | Linder |
| 5,283,520 | A | | 2/1994 | Martin et al. |
| 5,512,821 | A | * | 4/1996 | Ando et al. .............. 324/225 |
| 6,593,737 | B2 | | 7/2003 | Crouzen et al. |
| 6,661,224 | B1 | * | 12/2003 | Linder .................. 324/227 |

OTHER PUBLICATIONS

PCT/ISA/210—International Search Report—Apr. 18, 2005.
PCT/ISA/237—Written Opinion of the International Searching Authority—Apr. 18, 2005.

* cited by examiner

*Primary Examiner*—Jay M Patidar
(74) *Attorney, Agent, or Firm*—Venable LLP; Eric J. Franklin

(57) ABSTRACT

A method for non-contact determination of sought properties of an object to be measured by using electromagnetic induction. An electromagnetic field is generated in a transmitter coil placed on one side of the object to be measured. The magnetic field penetrates through the object to be measured and is detected by a receiver coil placed on the other side of the object to be measured. A control coil is placed near the transmitter coil generating a change in the magnetic field of the transmitter coil. A field change in the detecting is detected in the control coil. The field is detected in the receiver coil. The difference in time is determined for the detection of the field change in the control coil and in the receiver coil, respectively. The time of penetration through the object to be measured is determined, and the thickness or electrical conductivity of the object to be measured is determined therefrom.

17 Claims, 2 Drawing Sheets

METHOD AND A DEVICE FOR NON-CONTACT ELECTROMAGNETIC MEASUREMENT OF PROPERTIES OF OBJECTS

CROSS-REFERENCE TO RELATED APPLICATIONS

This application claims priority to Swedish patent application 0303610-0 filed 31 Dec. 2003 and is the national phase under 35 U.S.C. § 371 of PCT/SE2004/001983.

TECHNICAL FIELD

The present invention relates primarily to non-contact measurement of dimensions and properties such as, for example, resistivity of an object. The invention relates specifically to non-contact measurement that utilizes electromagnetic induction and measures on electrically conductive but substantially non-magnetic objects such as, for example, metal products.

One particular field of application is thickness measurement in the manufacture of metal sheets, metal strip, etc., and, for example, where it is necessary to continuously measure the thickness of the sheet to be able to increase the final quality of the sheet or strip.

The invention may also be used for measuring non-metallic, but electrically conductive, objects.

The invention is especially suited for non-contact and simultaneous measurement of thickness and electrical properties of a thin metallic and non-magnetic material.

BACKGROUND OF THE INVENTION

Measurement of dimensions and properties of metal products is of vital importance in the metal industry of today. To be able to control the end products to the desired quality in the manufacturing processes, it is of great importance for the continuous measurement of certain quantities to be correct and reliable. This particularly applies to the manufacture of sheet or strip where, for example, the thickness is of vital significance. The technique that is used today is normally based on light or radiation or mechanical contact.

One such known method for non-contact measurement of the thickness of a sheet is to irradiate it with radioactive radiation or with X-ray radiation and then measure the radiation absorption of the sheet. This absorption is dependent on, among other things, the thickness of the sheet and hence constitutes a primary measured value of the thickness of the object to be measured. The measured value is, however, influenced by the material composition of the object to be measured, so the accuracy of measurement is not sufficiently good.

Known techniques are also sensitive to disturbances from the surrounding environment and are difficult to use when a high material quality is aimed at. A new fundamental measurement technology, which does not possess these deficiencies, is therefore desirable.

One such technique is inductive measurement technique. This has long been proposed as a possible measurement technique for measuring dimensions and properties of metals. The oldest patents in the field date back as early as 1920. However, this technique has met with limited success and it was not industrially accepted until the technique was further developed.

The measurement of, for example, thickness proved to be too dependent on material. With the technique disclosed, for example, in U.S. Pat. No. 5,059,902 and SE 517293, industrially successful measuring equipment could suddenly be designed, manufactured and used. These various types of measuring equipment have proved to work well and to be without the deficiencies from which the prior art measurement technique suffered.

However, also this new technique has proved to involve certain drawbacks. One disadvantage is, for example, that it has not been possible to use it for measurement on really thin sheets with thicknesses down to about 0.1 mm for copper and aluminium, that is, metal foil, and for somewhat larger thicknesses for metals with higher electrical resistivity. This is a significant drawback since an industrial measurement technique of this kind should be generally applicable and capable of being used for measuring on objects/sheets of all available thicknesses so as to avoid the need of installing and using several different types of measuring equipment.

With further developed technique, it has been found to be possible, using electromagnetic technique, to measure also really thin sheets. One problem when measuring on very thin sheets, such as metal foils, is that the time of penetration of the magnetic fields, that is, the time it takes for a field change to penetrate through an object to be measured and be detected on the other side, is very short and hence in practice difficult to measure reliably using current technology. The reason for this is that the time of penetration is so short that it may be easily disturbed by other delays in the measuring system. For example, a certain delay in the electronic components of the measuring device itself always occurs.

OBJECTS AND MOST IMPORTANT CHARACTERISTICS OF THE INVENTION

One problem with the prior art is that the delay that arises when measurement is carried out in an electric/electronic system is not only dependent on the actual time of penetration but is also influenced by delays in the various electronic circuits and components of the measuring equipment. When the time of penetration is long, as for thicker sheets, this "electronic time delay" constitutes no decisive problem, since it is considerably shorter than the time of penetration. When the time of penetration is very short, for example for thin materials, a problem arises in that the electronic time delay becomes as long as, or longer than, the time of penetration of the field change in the object to be measured, the sheet. To be able to measure with sufficient accuracy, the electronic delay time must be known and a technique for handling this must be created. This is of decisive importance for permitting measurement on thin sheets.

Also when using the measurement technique according to U.S. Pat. No. 5,059,902 and SE 517293, a problem exists, when the highest accuracy is desired, in connection with delays in electronic circuits.

It is an object of the present invention to solve the above-mentioned problems and to suggest a measuring device which, with high accuracy, is capable of determining the thickness of a metallic object to be measured.

Another object of the invention is to solve, in all essentials, the measurement problem of being able to measure also thin sheet with the same type of equipment as is used in, for example, SE 517293. In case of very thin sheets, the problem of correctly calculating the time of penetration arises, in that delays in the electronics necessary for measurement are of the same order of magnitude as this time of penetration and that these two times cannot be separated.

This problem is solved, according to the invention, by the following method steps:
- placing a control coil 5 near the transmitter coil 3,
- generating a change in the magnetic field of the transmitter coil 3,
- detecting the field change in the control coil 5,
- detecting the field change in the receiver coil 4,
- determining the difference in time for detecting the field change in the control coil 5 and in the receiver coil 4, respectively,
- determining the time of penetration T2 through the object 2 to be measured, and
- determining therefrom the thickness or electrical conductivity of the object 2 to be measured.

The invention also relates to a device for non-contact determination of one or more sought properties of an object 2 to be measured, such as its geometrical dimension or electrical conductivity, comprising at least one transmitter coil 3 and at least one receiver coil 4 located in spaced relationship to each other, as well as means for generating a changeable magnetic field in the transmitter coil 3 and means for detecting a voltage S4 induced in the receiver coil 4.

The measuring device comprises arranging a control coil 5 to detect a change of the magnetic field generated in the transmitter coil 3,
- arranging means to detect the difference in time between the signals S5 and S4 from the control coil 5 and the receiver coil 4 which are generated by the change of magnetic field in the transmitter coil 3,
- arranging means 18, 19 to detect the maximum voltage S4max induced in the receiver coil 4, and
- arranging means to calculate, from these values, the thickness or electrical conductivity of the object to be measured 2.

The new technique thus implies that receiver and transmitter coils are located on opposite sides of the object to be measured and that the measuring device measures, as a basic quantity, the time it takes for the sudden field change, generated by the transmitter coil, to penetrate through the sheet and induce a voltage in the receiver coil, the so-called time of penetration.

The invention is particularly suitable to use in those cases where the field change is created by a step-by-step change of the supply current to the transmitter coil, for example a sudden cut-off of the supply current. In this context, time delay in the system is easily measurable as the time that elapses from the current cut-off until a change is detected in the measurement. This time delay is measured both in the receiver coil and in an extra control coil placed in the vicinity of the transmitter coil and the difference in time in these two cases is a measure of the time of penetration of the field through the object to be measured.

BRIEF DESCRIPTION OF THE ACCOMPANYING DRAWINGS

The invention will be described in greater detail below with reference to the accompanying figures.

FIG. 5 shows a simple flow chart of the method according to the invention.

DESCRIPTION OF THE PREFERRED EMBODIMENTS OF THE INVENTION

Figure 1:
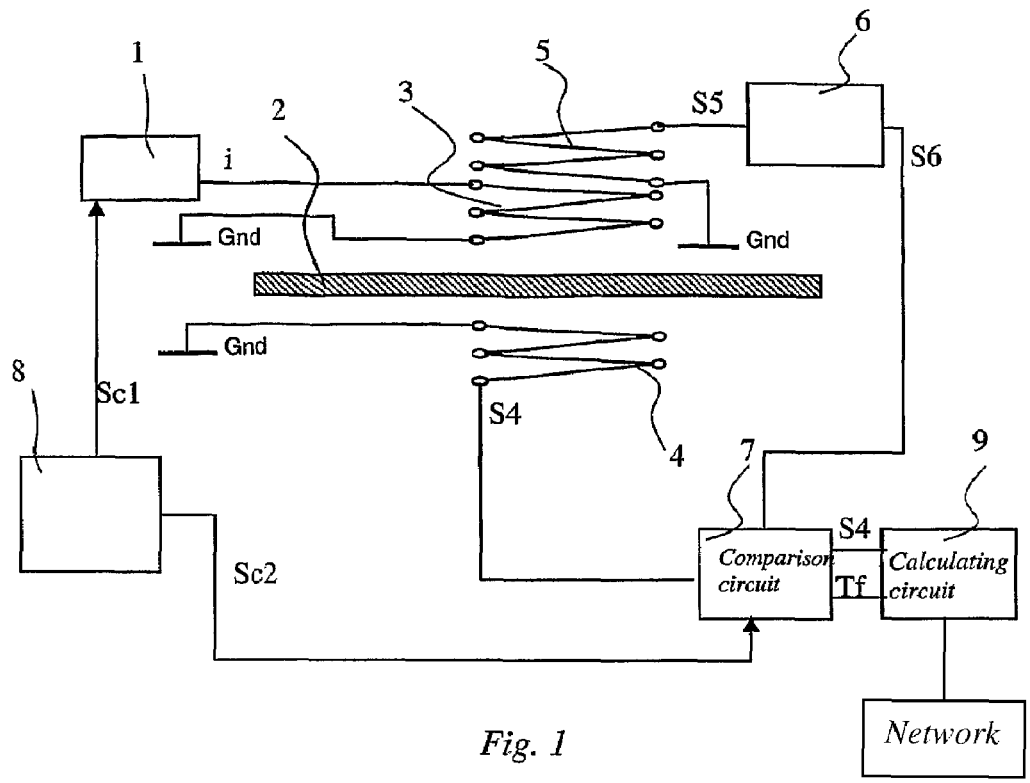
FIG. 1 shows an explanatory sketch of a measuring device according to the invention.

FIG. 1 is a sketch showing the principle of a measuring device 1 according to the invention. An object to be measured, here a sheet 2, is placed between a transmitter coil 3 and a receiver coil 4. The transmitter coil 3 is fed with a time-varied current, i, from a current-supply circuit 1. This time-varied current i is controlled from a time-control circuit 8 with a control signal Sc1. The circuits 1 and 8 are arranged such that the intended time variation of the supply current i is obtained.

The time-varying current gives rise to a similarly time-varied magnetic field around the transmitter coil 3. The receiver coil 4, on the other side of the sheet 2, detects the changes in the magnetic field penetrating through the sheet 2 by inducing a voltage, proportional to the change, in the receiver coil 4.

The time it takes for a field change to penetrate through the sheet 2 is a primary measured value that is needed to calculate the sought properties of the sheet 2, for example thickness and the electrical conductivity.

In the vicinity of the transmitter coil 3, preferably immediately outside the transmitter coil (3) in relation to the object (2) to be measured, and thus on the same side of the object (2) to be measured, a control coil 5 is placed, which detects any field changes in the vicinity of the transmitter coil 3. The induced voltage, the output signal S5, from this control coil 5 is filtered in a filter circuit 6 in such a way that its voltage level is essentially the same as that of the voltage out of the receiver coil 4. The control coil may advantageously be placed directly at the transmitter coil (3).

The two signals S4 and S6, from the receiver coil 4 and from the filter circuit 6, are compared in a comparison circuit 7, a time comparison. The two signals S4 and S6 are thus compared here in order to detect any time displacement between them, the so-called time delay. As a timely starting-point for this measurement, a control signal Sc2 from the time-control circuit 8 is used, which is derived from the same time-control circuit 8 as the control signal Sc1 for the supply current i. The timely starting-point for the timely comparison of the signals S4 and S6 will thus coincide with the timely starting-point for the change of supply current i to the transmitter coil 3.

In the comparison circuit 7, an unwanted delay time Tf is determined, which is dependent on delays in the electronics components. This delay time and the signal from the receiver coil are led to a calculating circuit where the thickness and/or electrical conductivity are/is calculated, taking into account unwanted delays in the circuits/the system.

The time delay in a measuring device, for example according to FIG. 1, may arise for several reasons. This is exemplified in the diagrams according to FIGS. 2A-C. In this case, a current is illustrated which varies in time by suddenly going from one value to another (see FIG. 2A), in this case from a constant value down to zero. The diagram shows the current i, that is, the current that comes from the current-supply circuit 1 in FIG. 1. At a certain time, the start time t1, the current-supply circuit 8 cuts off the current supply to the transmitter coil 3, but because of delays in the current-supply circuit 1, another short period of time T1 elapses until the current is really cut off. Typically, it may be a question of 20 ns.

The field change that occurs due to the current change being delayed and measured in the receiver coil 4 is shown in FIG. 2B. This delay is composed and consists of: a delay in the transmitter coil 3, T3; a delay from the receiver coil 4, T4; and a delay from the object to be measured, the sheet 2, T2. A change of the magnetic field and thus an induced voltage is obtained at a time t4.

The diagram according to FIG. 2C shows the delays in the circuit that comprises the control coil 5 and the filter circuit 6. If it is assumed that the filter circuit 6 itself does not contribute a delay, the total delay in this circuit will be the delay in the transmitter coil 3, T3, and the delay in the control coil 5, T5. An induced voltage arises here at a time t5. The receiver coil 4 and the control coil 5 are designed with the same time constant, so the sought delay time is obtained by detecting/measuring in the comparison circuit 7 the difference between the delays in the two signal circuits. The unwanted delay, the delay that is associated with delays in coils, and other electronics components, is equal to the delay that is measured in the signal S5, that is, Tf.

Figure 2:
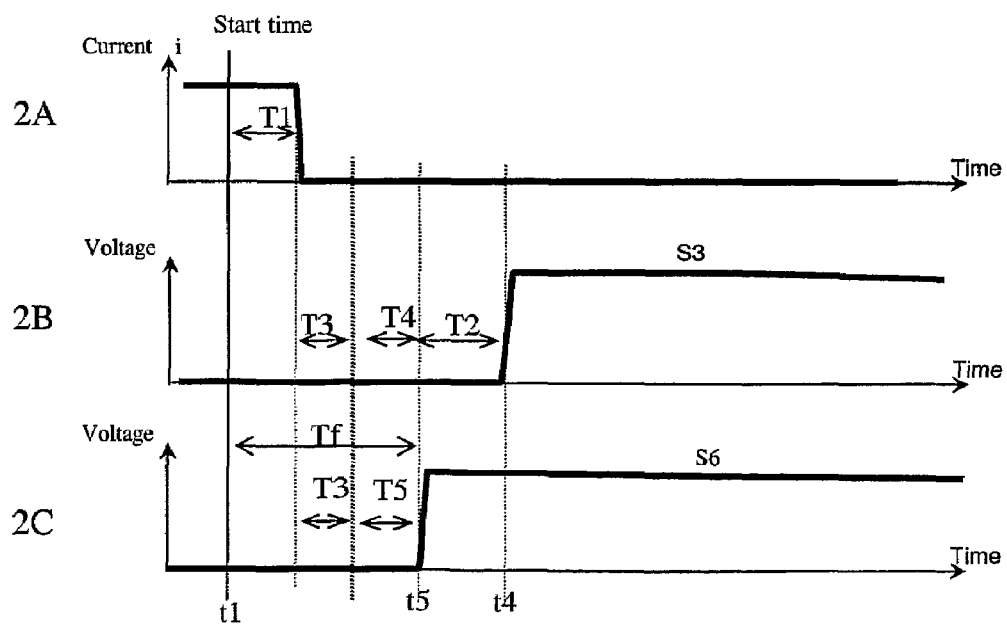
FIG. 2 shows different diagrams illustrating time delays of different signals.

The time comparison in the comparison circuit 7 and the calculation in the calculating circuit 9, according to FIG. 1, may be carried out in one single calculating circuit according to the principles described in connection with FIG. 1 and FIG. 2.

The elementary sketch according to FIG. 1 illustrates a case where the signal S4 is led direct from the receiver coil 4 to the comparison circuit 7. In certain measurement cases, however, it is required that the signal be amplified in amplifier circuits before it can be handled by the comparison circuit. Delays in these amplifier circuits will then be included in the delay time T4 of the receiver. In these cases, corresponding amplifier circuits are used for handling the signal S6 and also T5 is influenced in a corresponding way.

Figure 3:
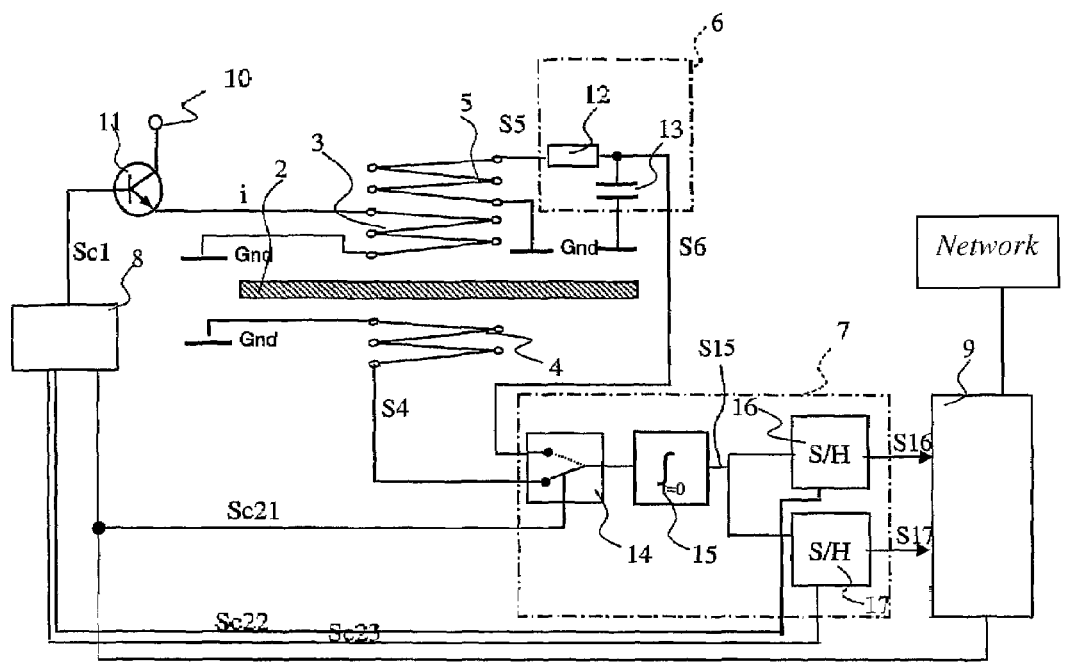
FIG. 3 shows a circuit solution for a preferred embodiment of the invention.

According to a preferred embodiment of the invention, shown in FIG. 3, the transmitter coil 3 is fed from a constant current source 10 via a transistor 11. The transistor 11 is controlled by a control circuit 8 in such a way that the transistor 11 is first open and carries current for a period of time sufficiently long for the magnetic field from the transmitter coil 3 to have time to penetrate through the sheet 2. Thereafter, the current supply is cut off.

The field change, which is a direct consequence of this sudden cut-off, penetrates through the sheet 2 and induces a voltage in the receiver coil 4. At the same time, the sudden field change in the transmitter coil 3 induces an induced voltage S5 in the control coil 5. This voltage S5 is filtered in a passive filter 6, consisting of a resistor 12 and a capacitance 13. The output signal S6 from this passive filter 6 and the output signal S4 from the receiver coil 4 are treated alternately, every other time the transistor 11 switches off the current, in that an analog switch 14 in the comparison circuit 7 alternately selects the signal S4 from the receiver coil 4 and the signal S6 from the filter 6, which is really the signal S5 from the control coil 5. The control of the switch 14 takes place via a control signal Sc21 from the control circuit 8.

In the comparison circuit 7, the signals are led alternately from the switch 14 to an integrator 15 that starts integrating when the transistor 11 switches off the current. The output signal S15 from the integrator 15 is then led to two so-called Sample and Hold circuits (S/H circuits) 16, 17, which are also controlled by the control circuit 8 via the control signals Sc22 and Sc23. These control signals are so adapted that two values of the signal S15 are retained at two different times in the two S/H circuits.

By selecting holding times for the S/H circuits 16, 17 which lie relatively close to the time after the field change has penetrated through the sheet 2—one of these holding times lying at a time t16 relatively close to the time after the field change has penetrated through, and the other holding time lying at a time t17 thereafter—the unwanted delay time Tf may be calculated in a simple manner, when the signal S6 of the control coil is connected, as:

$$Tf = t16 - S16 \times (t17 - t16)/(S17 - S16) - t1$$

Then, when the signal from the measuring coil S4 is connected, the actual time of penetration for the change in the sheet T2 may be calculated from:

$$T2 = t16 - S16 \times (t17 - t16)/(S17 - S16) - t1 - Tf$$

The above calculations are carried out in a calculating circuit 9.

Figure 4:
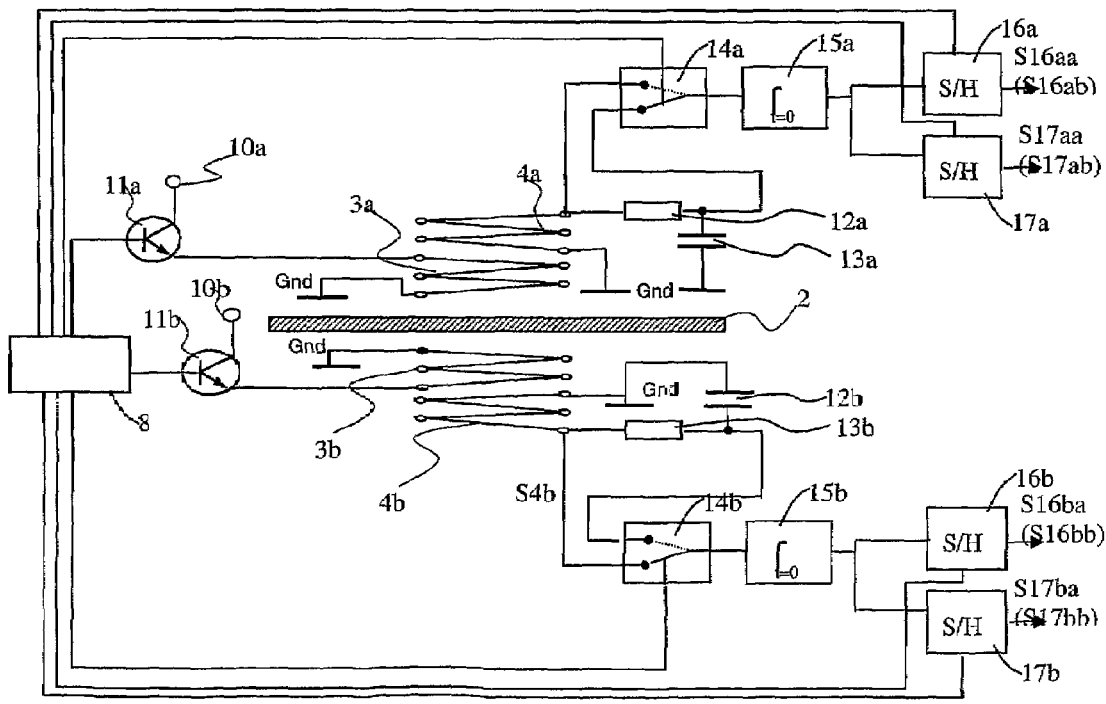
FIG. 4 shows another embodiment according to the invention with a doubled circuit solution.

An additional embodiment of the invention is shown in FIG. 4. In this case, two identical sets of circuits are arranged on respective sides of the object 2 to be measured, in the following called a- and b-sides. The control circuit 8 is, however, common to both circuits and controls the entire measuring device.

Current from a constant current source 10a is supplied via a transistor 11a to a transmitter coil 3a. At the stage described here, the transistor 11a is active, that is, it carries current, and the transistor 11b is passive, that is, it is cut off and not current-carrying. After supplying constant current for a certain period of time, the transistor 11a is suddenly switched off by the output signal from the control circuit 8 adopting a low level. After the current supply to the transmitter coil 3a has been cut off, the voltage induced in the receiver coil 4b on the other side of the object to be measured, the sheet 2, is detected. This is done by the analog switch 14b passing the signal S4b from the receiver coil 4b to the integrator 15b, where it is integrated. The resultant output signal S15b from the integrator 15b is then passed to the inputs of the two S/H circuits 16b, 17b, and the time for the change t4ba is then calculated from the values of the output signals S16ba, S17ba. In the same way, for the a-side, the time t5aa for change is at the same time calculated in the sensing coil 4a from the signals S16aa and S17aa.

After the a-side or the a-circuit has generated the magnetic field, that is, has been a current-generating side, the control is switched to the b-side or the b-circuit and the process as above is repeated. The times for change are now calculated in a corresponding way from the signals S16ab, S17ab, S16bb, S17bb as t4ab and t5bb.

Finally, the actual delay time FTv for the penetration of the magnetic field through the object 2 to be measured, the delay time through the object to be measured, that is, compensated for delays in electronics and coils, is obtained from the following relationship:

$$T2 = (t4ba + t4ab - t5aa - t5bb)/2$$

Where:

$$t4ba = t16 - S16ba*(t17 - t16)/(S17ba - S16ba)$$

$$t4ab = t16 - S16ab*(t17 - t16)/(S17ab - S16ab)$$

$$t5aa = t16 - S16aa*(t17 - t16)/(S17aa - S16aa)$$

$$t5bb = t16 - S16bb*(t17 - t16)/(S17bb - S16bb)$$

and where t16 and t17 are preset times for the sample and hold amplifiers. The calculation as above is carried out in a calculating circuit as the one shown in FIG. 3.

The method according to the invention may, at least partly, be carried out with the aid of program codes run in a processor or in a computer, and these program codes may be stored on a computer-readable medium such as a hard disk, a diskette, a CD-ROM, other movable memory, etc. The program codes may be at least partly transmitted via a network 18, such as, for example, the internet.

One important aspect of this invention, which is primarily intended to be used for measuring on thin sheet, is that the coils described in connection with FIGS. 1, 3 and 4 may also be used for measuring on thicker sheet by means of any of the inductive techniques which have been described as new. So, coils that are used for measuring thicker sheet according to SE 517 293 may be given a different use, for example according to FIG. 4, by changing, depending on sheet thickness, the feeding to transmitter coils and the connection of receiver coils. In the case of thick sheet, the transmitter coils 3a and 3b (FIG. 4) are then fed simultaneously and in opposite directions, while at the same time the two receiver coils 4a and 4b are connected as receiver coils with the aid of switches 14a and 14b. Then, when the arrangement is to be used for thin sheet, connection in accordance with the description referring to FIG. 4 is selected.

Although the invention has been described above by means of a few embodiments, the invention is not, of course, limited to these; other embodiments and variants are feasible within the scope of protection of the claims. Thus, it is conceivable that the delay times may be calculated using mathematical formulae that are partly different from those shown here.

It is also possible to use the transmitter coil as a control coil in those cases where the transmitter coil is not active, that is, when the current through the transistor is cut off (see, e.g., FIG. 1). When the transistor is switched off, the transmitter coil is disengaged from the current supply and may then be used as a control coil or as a receiver coil.

The invention claimed is:

1. A method for non-contact determination of sought properties of an object to be measured, by using electromagnetic induction, the method comprising:
    generating a first electromagnetic field in a first transmitter coil placed on a first side of the object to be measured,
    detecting the first electromagnetic field penetrating through the object to be measured by a first receiver coil placed on a second side of the object to be measured,
    placing a first control coil near the first transmitter coil,
    generating a change in the first electromagnetic field of the first transmitter coil,
    detecting the field change in the first control coil,
    detecting the field change in the first receiver coil,
    determining a first difference in time for the detection of the field change in the first control coil and in the first receiver coil, respectively,
    determining a time of penetration through the object to be measured, and
    determining from the time of penetration the thickness or electrical conductivity of the object to be measured.

2. The method according to claim 1, wherein the control coil is located on the same side as the transmitter coil in relation to the object to be measured.

3. The method according to claim 1, wherein the time of penetration through the object to be measured is determined based on the time for detection of the field change in the control coil, and the time for detection of the field change in the receiver coil.

4. The method according to claim 1, further comprising:
    generating a second electromagnetic field in a second transmitter coil placed on the second side of the object to be measured;
    detecting the second electromagnetic field penetrating through the object to be measured by a second receiver coil placed on the first side of the object to be measured;
    placing a second control coil near the second transmitter coil;
    generating a change in the second electromagnetic field of the second transmitter coil;
    detecting the field change in the second control coil;
    detecting the field change in the second receiver coil; and
    determining a second difference in time for the detection of the field change in the second control coil and in the second receiver coil, respectively;
    wherein the calculation of the time of penetration through the object to be measured is equal to $(t4ba+t4ab-t5aa-t5bb)/2$, where $t4ba$, $t4ab$, $t5aa$ and $t5bb$ represent differences in determined times for the field changes between the first control coil, first receiver coil, second control coil and second receiver coil.

5. The method according to claim 1, wherein the voltage induced in the receiver coil is measured at two different times after the magnetic field in the transmitter coil has suddenly changed.

6. The method according to claim 1, wherein the thickness or electrical conductivity of the object to be measured is calculated on the basis of the time of penetration and the maximum voltage induced in the receiver coil.

7. The method according to claim 1, wherein the thickness or electrical conductivity of the object to be measured is calculated on the basis of the reciprocal value of the product of the square of the maximum voltage induced in the receiver coil and the time of penetration.

8. The method according to claim 1, wherein the voltage induced in the receiver coil is integrated and that the thickness or electrical conductivity of the object to be measured is calculated on the basis of this integrated signal.

9. The method according to claim 1, wherein the voltage induced in the receiver coil is integrated and that the thickness or electrical conductivity of the object to be measured is calculated on the basis of the value of this integrated signal at at least two different times.

10. The method according to claims 1, wherein the sought properties comprise a geometrical dimension of the object or an electrical conductivity of the object.

11. A measuring device for non-contact determination of one or more sought properties of an object to be measured, comprising:
    at least one transmitter coil and at least one receiver coil located spaced from each other,
    a magnetic field generator configured to generate a changeable magnetic field in the transmitter coil,
    a detector configured to detect a voltage induced in the receiver coil,
    a control coil arranged to detect a change in the magnetic field generated in the transmitter coil,
    a detector configured to detect a difference in time between signals from the control coil and the receiver coil which are generated by the change in magnetic field in the transmitter coil,
    a detector configured to detect a maximum voltage induced in the receiver coil, and
    a calculator configured means to calculate, from said difference in time and said maximum voltage, the thickness or electrical conductivity of the object to be measured.

12. The measuring device according to claim 11, wherein the control coil is arranged on a same side of the object to be measured as the transmitter coil.

13. The measuring device according to claim 11, further comprising:
    an integrator to integrate a voltage signal induced in the receiver coil.

14. The measuring device according to claim 11, further comprising:
   circuits arranged to measure the voltage induced in the receiver coil at two different times after the time for interruption in the transmitter coil.

15. The measuring device according to claim 11, wherein the properties to be measured comprise a geometrical dimension or an electrical conductivity of the object.

16. A computer program product, comprising:
   a computer readable medium; and
   data code recorded on the computer readable medium executable by a processor for carrying out the steps of
   generating an electromagnetic field in a transmitter coil, placed on one side of the object to be measured,
   detecting the magnetic field penetrating through the object to be measured by a receiver coil placed on the other side of the object to be measured,
   placing a control coil near the transmitter coil,
   generating a change in the magnetic field of the transmitter coil,
   detecting the field change in the control coil,
   detecting the field change in the receiver coil,
   determining the difference in time for the detection of the field change in the control coil and in the receiver coil, respectively,
   determining the time of penetration through the object to be measured, and
   determining therefrom the thickness or electrical conductivity of the object to be measured.

17. The computer program according to claim 16, wherein the data code if further for carrying out the step of at least partly transmitting the data code via a network.

* * * * *